United States Patent [19]

Ohikata et al.

[11] Patent Number: 5,061,074
[45] Date of Patent: Oct. 29, 1991

[54] APPARATUS FOR INSPECTING BOTH SIDES OF TAPE OR SHEET

[75] Inventors: Naoharu Ohikata; Toshiro Matsubara; Jiro Ohno, all of Tokyo, Japan

[73] Assignee: Nippon Steel Corporation, Tokyo, Japan

[21] Appl. No.: 422,491

[22] Filed: Oct. 17, 1989

[30] Foreign Application Priority Data

Oct. 17, 1988 [JP] Japan .................. 63-259500

[51] Int. Cl.$^5$ .................................. G02B 27/02
[52] U.S. Cl. .......................... 356/390; 359/372; 359/376
[58] Field of Search ............ 350/511; 356/390, 388

[56] References Cited

U.S. PATENT DOCUMENTS

| | | | |
|---|---|---|---|
| 3,421,806 | 1/1969 | Weber | 350/502 |
| 3,752,589 | 8/1973 | Kobayashi | 350/511 |
| 3,900,244 | 8/1975 | Wiesler et al. | 350/511 |
| 4,619,503 | 10/1986 | Reinheimer et al. | 350/511 |
| 4,827,376 | 5/1989 | Voss | 361/388 |

FOREIGN PATENT DOCUMENTS 3323836  1/1985  Fed. Rep. of Germany ...... 356/390

OTHER PUBLICATIONS

Jackson et al., "Dual Microscope System", *IBM Technical Disclosure Bulletin*, vol. 21, No. 8 (Jan. 1979), pp. 3129–3130.

*Primary Examiner*—Richard A. Rosenberger
*Attorney, Agent, or Firm*—Wenderoth, Lind & Ponack

[57] ABSTRACT

An apparatus for inspecting the top and bottom surfaces of a tape or sheet has a device to magnify the surface of the tape or sheet, with its objective lens disposed to face the top surface of the tape or sheet. The apparatus also has an optical transmittion system that transmits an image of the bottom surface of the tape or sheet through a focusing unit and four reflectors, each of which is adapted to bend the path of light rays 90 degrees. Of the four reflectors, one that faces the objective lens is retractable from the light-ray path in the optical transmission system. The reflector facing the objective lens may be a half-coated mirror. Fixed in the light-ray path in the optical transmission system, the half-coated mirror is not retractable.

8 Claims, 2 Drawing Sheets

APPARATUS FOR INSPECTING BOTH SIDES OF TAPE OR SHEET

BACKGROUND OF THE INVENTION

1. Field of the Invention

This invention relates to an apparatus for inspecting both sides of a tape or a sheet.

This invention is applicable to an apparatus that magnifies and visually inspects both sides of a transparent, translucent or opaque tape or sheet, such as a TAB tape and a flexible printed-circuit board.

2. Description of the Related Art

Tape automated bonding (TAB) is one of the automatic bonding processes for semiconductor devices. In TAB, a semiconductor chip is attached, bonded and sealed on each frame of a long TAB tape (U.S. Pat. No. 4,827,376 V. V. Scott). A TAB tape is made of transparent or translucent plastics, such as polyimide, with a large number of extra-fine wires of copper or gold- or tin-plated copper laid on the surface.

Before attaching semiconductor devices, each TAB tape is inspected for defects. Each frame of a TAB tape, intermittently paid off from a reel, is visually inspected under a microscope for broken leads, deformation and other defects.

Two-side wired TAB tapes must be inspected on both sides.

With the conventional inspection apparatus, however, one side of a tape is first inspected throughout. Then, the tape is reversed for the inspection of the other side. Namely, the TAB tape passes through the inspection apparatus twice. This has decreased the efficiency of the inspection work, increased chances of damaging the TAB tape and lowered the production yield.

Similar problems have been encountered in the two-side inspection of flexible printed-circuit board, as well.

SUMMARY OF THE INVENTION

The object of this invention is to provide an apparatus for inspecting both sides of a tape or sheet, such as a TAB tape, in a single pass.

An apparatus to inspect both sides of a tape or sheet according to this invention is equipped with a device to magnify the surface of the tape or sheet, with the objective lens disposed to face the top surface thereof. The apparatus also has an optical transmission system to send an image of the bottom surface of the tape or sheet to the objective lens through a focusing unit and four reflectors, each of which bends the path of light rays 90 degrees. One of the reflectors facing the objective lens is retractable from the path of light rays in the optical transmission system.

The focusing unit produces a substantially equimultiple real image of the bottom surface of the tape or sheet at the point where the distance between the objective lens and the image surface of the light-ray path in the optical transmission system is substantially equal to the distance between the objective lens and the top surface of the tape or sheet under examination. It is not necessary for the two distances to be exactly the same, so far as the depth of focus of the optical system of the magnifying device tolerates. Also, it is unnecessary for the images of both sides to be of exactly the same size if there is no need to compare the top and bottom surfaces of the tape or sheet. The focusing unit comprises an image forming lens, or a combination of an image forming lens plus a relay lens or a field lens, or a combination of an image forming lens plus a relay lens and a field lens. The reflector facing the objective lens can be retracted from the light-ray path in the optical transmission system by, for example, means of a movable frame that is reciprocated by the action of an air cylinder, hydraulic cylinder or electric motor.

A microscope or a projector is used as the magnifying device. The microscope or projector may be of the stereoscopic type. The reflectors are reflecting mirrors, half-coated mirrors or prisms disposed at an angle of 45 degrees relative to the light-ray path.

The inspection apparatus may also have two sets of lighting units adapted to individually illuminate the top and bottom surfaces of the tape or sheet. The lighting units may be retractable from the light-ray path when unnecessary by the same mechanism as is used with the reflector as described previously. Fluorescent or incandescent lights are used as the lighting units. The lighting units must be such as will uniformly illuminate the surface of the tape or sheet, without obstructing the field of vision of the magnifying device.

When inspecting the top surface of a tape or sheet using the apparatus of this invention just described, the reflector facing the objective lens is retracted from the light-ray path in the optical transmission system. Consequently, the inspector can directly observe the top surface of the tape or sheet through the magnifying device. If the tape or sheet is transparent or translucent, the top surface is illuminated brightly, whereas the bottom surface is either darkened or illuminated with a back light of such color as pale blue or green that does not irritate the eyes. This differential lighting permits observing the top surface alone, preventing the glaring of light from the bottom surface that might otherwise reach the eyes through the tape or sheet.

When the inspection of the top surface is complete, the reflector facing the objective lens is returned into the light-ray path. The focusing unit and four reflectors in the optical transmission system send an image of the bottom surface of the tape or sheet to the objective lens of the magnifying device, which enlarges the real image of the bottom surface of the tape or sheet focused by the focusing unit. Then, the bottom surface of the tape or sheet is illuminated brightly, whereas the top surface is either darkened or lighted dimly with a back light of pale color.

When the bottom surface of the tape or sheet is inspected, the distance between the objective lens and the image surface in the light-ray path in the optical transmission system is substantially equal to the distance between the objective lens and the top surface of the tape or sheet under examination. Thus, there is no need of focusing the magnifying device. Also, there is no need of readjusting the magnification of the magnifying device because the focused image of the bottom surface of the tape or sheet is substantially equimultiple.

Another preferred embodiment of this invention differs from the inspection apparatus just described in that the reflector facing the objective lens is a half-coated mirror, which is fixed in the light-ray path in the optical transmission system. Namely, this reflector, unlike the corresponding one described previously, is not refractable from the light-ray path.

In inspecting the top surface of the tape or sheet, the top surface of the tape or sheet is brightly illuminated, whereas the bottom surface is either darkened or illuminated with a back light of such color as pale blue or green. As this arrangement keeps the image of the bottom surface of the tape or sheet out of sight, the inspector can directly observe the top surface of the tape or sheet through the half-coated mirror and magnifying device.

When the top surface has been inspected, the bottom surface of the tape or sheet is brightly illuminated, whereas the top surface is either darkened or dimly lighted with a back light of pale color. The focusing unit and four reflectors in the optical transmission system send an image of the bottom surface of the tape or sheet to the objective lens of the magnifying device. In this case, the half-coated mirror functions as a reflecting mirror. The magnifying device enlarges the real image of the bottom surface produced by the focusing unit.

The inspection apparatus of this invention permits both sides of a tape or sheet to be inspected in a single pass. This results in increased inspection efficiency. Dispensing with such members as a movable frame and air cylinder, the apparatus employing a half-coated mirror offers additional advantages of compact design and economy.

DESCRIPTION OF THE PREFERRED EMBODIMENTS

Figure 1:
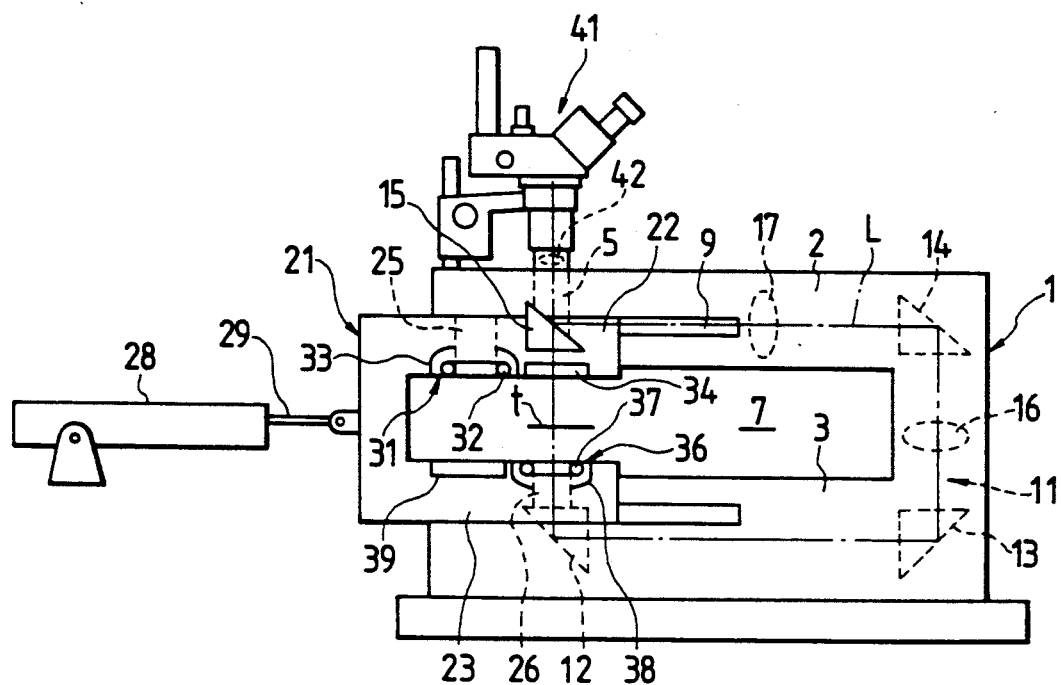
FIG. 1 is a front view.
Figure 2:
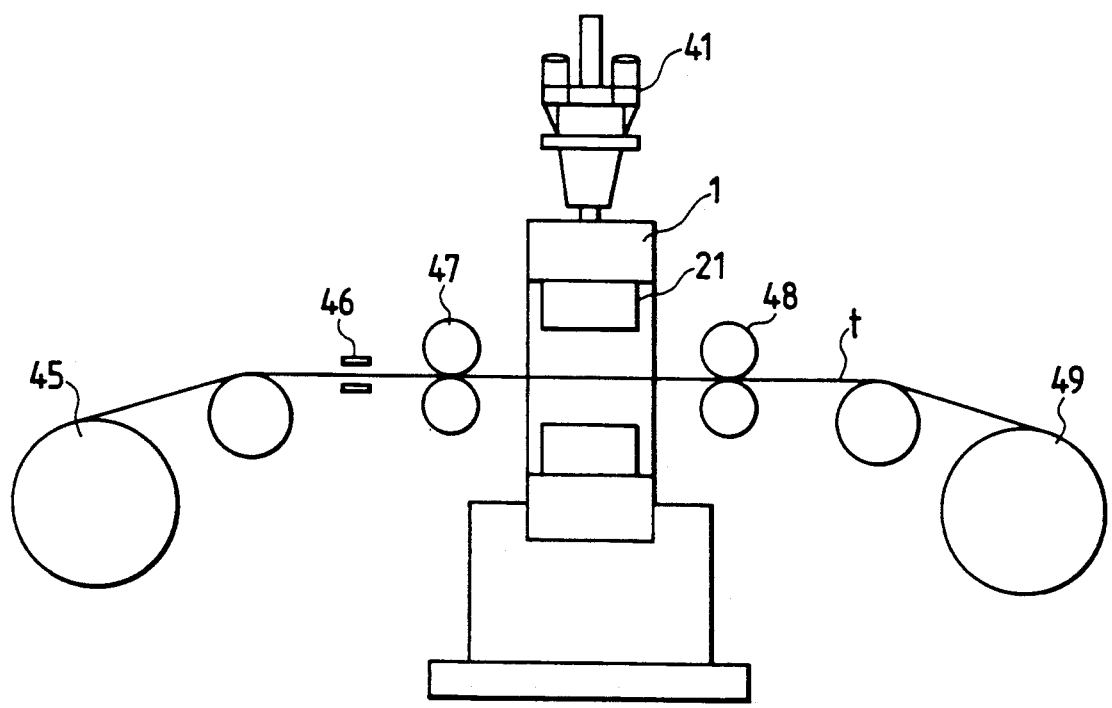
FIG. 2 is a side elevation of a TAB tape inspection apparatus according to this invention.

FIGS. 1 and 2 show a preferred embodiment of this invention; FIG. 1 is a front view and FIG. 2 is a side elevation of a TAB tape inspection apparatus.

As shown in the figures, a TAB tape inspection apparatus has a U-shaped housing 1. The housing 1 has a hollow space inside, in which an optical transmission system 11 described in the following is disposed. A through hole 5 is bored in an upper horizontal arm 2 of the housing 1. A TAB tape t horizontally passes through an opening 7 in the housing 1.

The housing 1 carries inside a first prism 12, a second prism 13 and a third prism 14 which make up a part of the optical transmission system 11 as shown in FIG. 1. The third prism 14 is roof-shaped to bilaterally reverse an image of the bottom surface of the TAB tape t. A focusing lens 16 is provided between the second prism 13 and the third prism 14, whereas a field lens 17 is provided on the exit side (the left side in the figure) of the third prism 14. The focusing lens 16 and the field lens 17 produce an equimultiple real image of the bottom surface of the TAB tape t on the exit side (the left side in the figure) of the field lens 17. The distance between an objective lens 42 of a stereoscopic microscope 41 and the image surface is equal to the distance between the objective lens 42 and the top surface of the TAB tape. Provision may also be made so that the focusing lens 16 produces the real image at the field lens 17.

Guide grooves 9 are cut in upper and lower horizontal arms 2 and 3 of the housing 1. A movable frame 21 is horizontally slidably fit in the guide grooves 9. A fourth prism 15 is fastened to an upper horizontal arm 22 of the movable frame 21. A pale blue back light 34 is attached immediately below the fourth prism 15. The pale blue back light 34 illuminates the top surface of the TAB tape t. A lighting unit 31 to uniformly illuminate the top surface of the TAB tape t is provided beside the back light 34. The lighting unit 31 comprises a ring-shaped light source 32 and a hemispherical shade 33. The shade 33 has an open top. A lighting unit 36 having a ring-shaped light source 37 and a hemispherical shade 38 is attached to a lower horizontal arm 23 of the movable frame 21 in such a manner as to face the fourth prism 15. A back light 39 is provided beside the lighting unit 36. Through holes 25 and 26 are bored in the upper and lower horizontal arms 22 and 23 of the movable frame 21, coaxially with the ring-shaped light sources 32, 37. A lighting unit 36 and back light 39 are analogous to the lighting unit 32 and back light 34 on the upper arm. A rod 29 of an air cylinder 28 is connected to a vertical portion of the movable frame 21.

A stereoscopic microscope 41 is mounted on the housing 1. The objective lens 42 of the stereoscopic microscope 41 is coaxial with the through hole 5 in the housing 1. An uncoiling reel 45, a TAB tape sensor 46 and feed rolls 47 are disposed in that order on the upstream side of the housing 1. The TAB tape sensor optically detects each frame of the TAB tape t paid off from the uncoiling reel 45. Downstream of the housing 1 are disposed feed rolls 48 and a take-up reel 49 in that order. Having teeth adapted to engage with sprocket holes in the TAB tape t, the feed rolls 47 and 48 exactly send forward the TAB tape t one frame after another.

Signals initiated by the TAB tape sensor 46 are input in a computer (not shown). Based on the signals from the TAB tape sensor 46, the computer controls the action of the air cylinder 28, uncoiling reel 45, feed rolls 47 and 48 and take-up reel 49.

The following paragraphs describe the method of inspecting a TAB tape t with the apparatus just described.

First, the uncoiling reel 45 pays off a TAB tape t one frame after another. When one frame of the TAB tape t reaches and stops at the inspection point, only the top surface thereof is inspected first. In this instance, the fourth prism 15 facing the objective lens 42 is retracted from the light-ray path L. The upper lighting unit 31 uniformly illuminates the top surface of the TAB tape t, whereas the lower back light 36 dimly lights the bottom surface thereof. This permits the inspector to directly observe the top surface of the TAB tape t through the stereoscopic microscope 41.

When the inspection of the top surface is complete, the fourth prism 15 facing the objective lens 42 is returned into the light-ray path L. The four prisms 12, 13, 14, 15, the focusing lens 16 and the field lens 17 of the optical transmission system 11 send an image of the bottom surface of the TAB tape t to the objective lens 42 of the stereoscopic microscope 41. The stereoscopic microscope 41 stereoscopically enlarges the real image of the bottom surface of the TAB tape t focused at the field lens 17 or on the exit side thereof. In this instance, the lower lighting unit uniformly illuminates the bottom surface of the TAB tape t, whereas the upper back light 34 dimly lights the top surface thereof.

When both sides have been thus inspected, the computer issues instructions to automatically actuate the air cylinder 28, uncoiling reel 45, feed rolls 47 and 48 and take-up reel 49 to proceed to the inspection of the next frame. Inspection continues, examining the top surface, bottom surface, bottom surface, top surface, top surface and so on of the TAB tape t.

Figure 3:
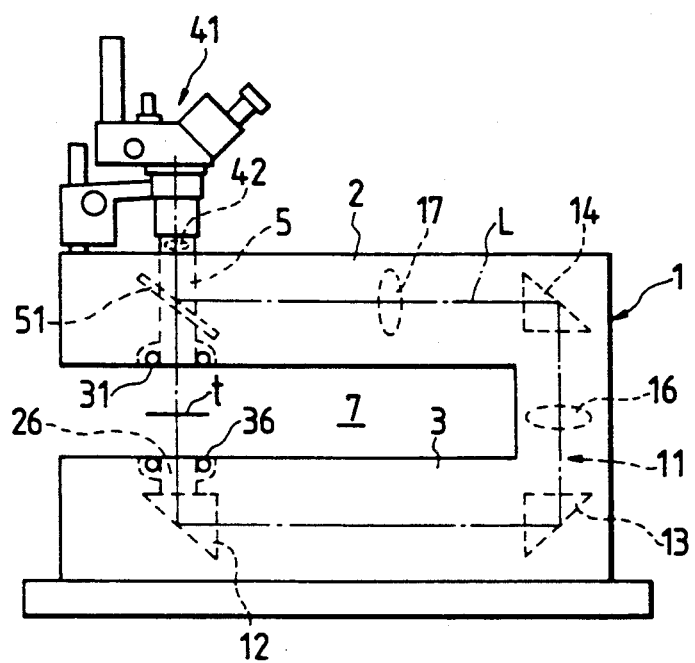
FIG. 3 is a front view of another TAB tape inspection apparatus according to this invention.

Now a second preferred embodiment of this invention will be described by reference to FIG. 3. Of the devices and members shown in FIG. 3, those analogous to ones shown in FIG. 1 are designated by the same reference characters, with detailed description thereof omitted.

As shown in the figure, the fourth reflector is a half-coated mirror 51, which is fastened to the upper horizontal arm 2 of the housing 1 at an angle of 45 degrees relative to a horizontal plane. The upper and lower lighting units 31 and 36 are coaxial with the through hole 5 and equipped with a light controller (not shown).

Using this apparatus, both sides of a TAB tape t are inspected as described in the following. In inspecting the top surface of the TAB tape t, the upper lighting unit 31 to illuminate the top surface is turned on, whereas the lower lighting unit 36 for the bottom surface is turned off. This keeps the image of the bottom surface out of the sight, whereby the inspector can directly observe only the top surface of the TAB tape t through the half-coated mirror 51 and the stereoscopic microscope 41. When the top surface has been inspected, the lower lighting unit 36 to illuminate the bottom surface of the TAB tape t is turned on, whereas the upper lighting unit 31 for the top surface is turned off. Then, the four reflectors 12 to 51, focusing lens 16 and field lens 17 of the optical transmission system 11 send an image of the bottom surface of the TAB tape t to the objective lens 42 of the stereoscopic microscope 41. In this instance, the half-coated mirror 51 serves as a reflecting mirror, thereby permitting the observation of the bottom surface alone.

This invention is by no means limited to the perferred embodiment described herein. The feed rolls 47 and 48 may be designed to be elevatable so that the focus of the stereoscopic microscope 41 relative to the TAB tape t may be adjusted by vertically moving the feed rolls 47 and 48. If provision is made to control the amount of light emitted by the lighting units 31 and 36, the TAB tape t may be inspected under the optimum lighting condition.

A douser or a shutter placed on the opposite side of the surface to be inspected in the second preferred embodiment described before permits an unblurred observation of the desired surface only. By illuminating both sides of the TAB tape t with lights of different colors, it becomes possible to simultaneously inspect the overlapped images thereof. This permits inspecting, for example, whether the leads on the surface agree with the through holes in the base layer of the TAB tape.

What is claimed is:

1. An apparatus for detecting defects in a top and bottom surface of a transparent or semitransparent tape or sheet material, comprising:

means for feeding a transparent or semitransparent material to be inspected;

means for producing image information of the surface of the material being inspected;

first image information transmitting means for transmitting image information of the top surface of the material fed by said feeding means to said image producing means;

second image information transmitting means for transmitting an image information of a bottom surface of the material fed by said feeding means to said image producing means;

first illuminating means for illuminating the top surface of the material fed by said feeding means;

second illuminating means for illuminating the bottom surface of the material fed by said feeding means; and actuating means for selectively actuating the first or second illuminating means;

wherein said image producing means comprises a stereoscopic microscope;

wherein said first illuminating means comprises a first uniformly illuminating lighting unit and a first non-eye-irritating back light of a pale blue or green color;

wherein said second illuminating means comprises a second uniformly illuminating lighting unit and a second non-eye-irritating back light of a pale blue or green color; and wherein said actuating means illuminates said first uniformly illuminating lighting unit and said second non-eye-irritating back light when the top surface of the material is being inspected and illuminates said first non-eye-irritating back light and said second uniformly illuminating lighting unit when the bottom surface of the material is being inspected.

2. The apparatus according to claim 1, wherein said second image information transmitting means includes four individual means for bending the path of the image information of the material being inspected 90 degrees each.

3. The apparatus according to claim 1, wherein said actuating means illuminates said first illuminating means brighter than said second illuminating means when the top surface of the material is being inspected.

4. The apparatus according to claim 1, wherein:

said actuating means illuminates only said first lighting unit when the top surface of the material is being inspected and illuminates only said second lighting unit when the bottom surface of the material is being inspected.

5. An apparatus for detecting defects in top and bottom surfaces of a transparent or semitransparent tape material, comprising:

means for intermittently conveying a transparent or semitransparent material in a direction;

means for producing image information of the surface of the material being inspected;

means for feeding an inspected area of the material conveyed by said conveying means to said image producing means;

first image information transmitting means for transmitting image information of the top surface of the material fed by said feeding means to said image producing means;

second image information transmitting means for transmitting image information of a bottom surface of the material fed by said feeding means to said image producing means;

first illuminating means for illuminating the top surface of the material fed by said feeding means;

second illuminating means for illuminating the bottom surface of the material fed by said feeding means; and means for selectively actuating the first or second illuminating means;

wherein said image producing means comprises a stereoscopic microscope;

wherein said first illuminating means comprises a first uniformly illuminating lighting unit and a first noneye-irritating back light of a pale blue or green color;

wherein said second illuminating means comprises a second uniformly illuminating lighting unit and a second non-eye-irritating back light of a pale blue or green color; and wherein said actuating means illuminates said first uniformly illuminating lighting unit and said second non-eye-irritating back light when the top surface of the material is being inspected and illuminates said first non-eye-irritating back light and said second uniformly illuminating lighting unit when the bottom surface of the material is being inspected.

6. The apparatus according to claim 5, wherein said second image information transmitting means includes four individual means for bending the path of the image information of the material being inspected 90 degrees each.

7. The apparatus according to claim 5, wherein said actuating means illuminates said first illuminating means brighter than that of said second illuminating means when the top surface of the material is being detected.

8. The apparatus according to claim 5, wherein:

said actuating means illuminates only said first lighting unit when the top surface of the material is being inspected and illuminates only said second lighting unit when the bottom surface of the material is being inspected.

* * * * *